(12) United States Patent
Ehlert

(10) Patent No.: US 10,076,592 B2
(45) Date of Patent: Sep. 18, 2018

(54) SYSTEM FOR ASPIRATING FLUIDS FROM A BODY USING NEGATIVE PRESSURE

(75) Inventor: Hilmar Ehlert, Hergiswil (CH)

(73) Assignee: MEDELA HOLDING AG, Baar (CH)

( * ) Notice: Subject to any disclaimer, the term of this patent is extended or adjusted under 35 U.S.C. 154(b) by 685 days.

(21) Appl. No.: 14/127,428

(22) PCT Filed: Jun. 14, 2012

(86) PCT No.: PCT/CH2012/000132
§ 371 (c)(1),
(2), (4) Date: Feb. 11, 2014

(87) PCT Pub. No.: WO2012/174672
PCT Pub. Date: Dec. 27, 2012

(65) Prior Publication Data
US 2014/0194835 A1    Jul. 10, 2014

(30) Foreign Application Priority Data

Jun. 23, 2011 (CH) .................................... 1064/11

(51) Int. Cl.
*A61M 1/00* (2006.01)
*A61M 27/00* (2006.01)
(Continued)

(52) U.S. Cl.
CPC ........ *A61M 1/0025* (2014.02); *A61M 1/0023* (2013.01); *A61M 1/0084* (2013.01); *A61M 2205/3344* (2013.01)

(58) Field of Classification Search
CPC ......... A61M 1/00; A61M 27/00; A61F 13/00; A61F 13/02
See application file for complete search history.

(56) References Cited

U.S. PATENT DOCUMENTS

| | | |
|---|---|---|
| 5,738,656 A | 4/1998 | Wagner |
| 2009/0157019 A1 | 6/2009 | Koch et al. |

(Continued)

FOREIGN PATENT DOCUMENTS

| | | |
|---|---|---|
| CN | 101227937 A | 7/2008 |
| CN | 101378795 A | 3/2009 |

(Continued)

OTHER PUBLICATIONS

Second Office Action, Chinese Patent Application No. 201280031000.7, dated Nov. 18, 2015, with an English Translation.

(Continued)

*Primary Examiner* — Tatyana Zalukaeva
*Assistant Examiner* — Ilya Treyger
(74) *Attorney, Agent, or Firm* — Marshall, Gerstein & Borun LLP

(57) ABSTRACT

A system for aspirating fluids from a body by means of negative pressure has: a drainage line for removing the fluid from the body, a fluid collection container connected to the drainage line and used to collect the aspirated fluid, a pump by which the negative pressure used to aspirate the fluid is generated in the drainage line, and an auxiliary line whose end near the body is in fluidic communication with an end, near the body, of the drainage line. In the system, an approximately closed circuit is present or can be generated which interconnects this pump, the auxiliary line, the drainage line and the fluid collection container and through which air or a liquid can be pumped, wherein the auxiliary line is usable for flushing the drainage line. This system prevents and removes obstructions in the drainage line and also permits a relatively accurate measurement of the negative pressure in the body cavity.

12 Claims, 1 Drawing Sheet

(51) Int. Cl.
*A61F 13/00* (2006.01)
*A61F 13/02* (2006.01)

(56) References Cited

U.S. PATENT DOCUMENTS

| | | |
|---|---|---|
| 2009/0163882 A1 | 6/2009 | Koch et al. |
| 2010/0204663 A1 | 8/2010 | Wudyka |
| 2011/0071415 A1 | 3/2011 | Karwoski et al. |

FOREIGN PATENT DOCUMENTS

| | | |
|---|---|---|
| JP | 2009520516 A | 5/2009 |
| JP | 2009525087 A | 7/2009 |
| WO | WO-03103747 A1 | 12/2003 |
| WO | WO 2004/037334 A1 * | 5/2004 |
| WO | WO-2004/037334 A1 | 5/2004 |
| WO | WO-2005/061025 A1 | 7/2005 |
| WO | WO-2007/013064 A1 | 2/2007 |
| WO | WO-2007067685 A2 | 6/2007 |
| WO | WO-2007087810 A2 | 8/2007 |
| WO | WO-2008/132215 A1 | 11/2008 |
| WO | WO 2009/089390 * | 7/2009 |
| WO | WO-2009/089390 A2 | 7/2009 |
| WO | WO-2010/126444 A1 | 11/2010 |
| WO | WO-2011/037524 A1 | 3/2011 |
| WO | WO-2012145612 A1 | 10/2012 |

OTHER PUBLICATIONS

International Preliminary Report on Patentability (including English translation of previously submitted Written Opinion) for International Application No. PCT/CH2012/000132, dated Dec. 23, 2013.
Written Opinion of the International Searching Authority for Application No. PCT/CH2012/000132, dated Jul. 30, 2012.
International Search Report for Application No. PCT/CH2012/000132, dated Jul. 30, 2012.

* cited by examiner

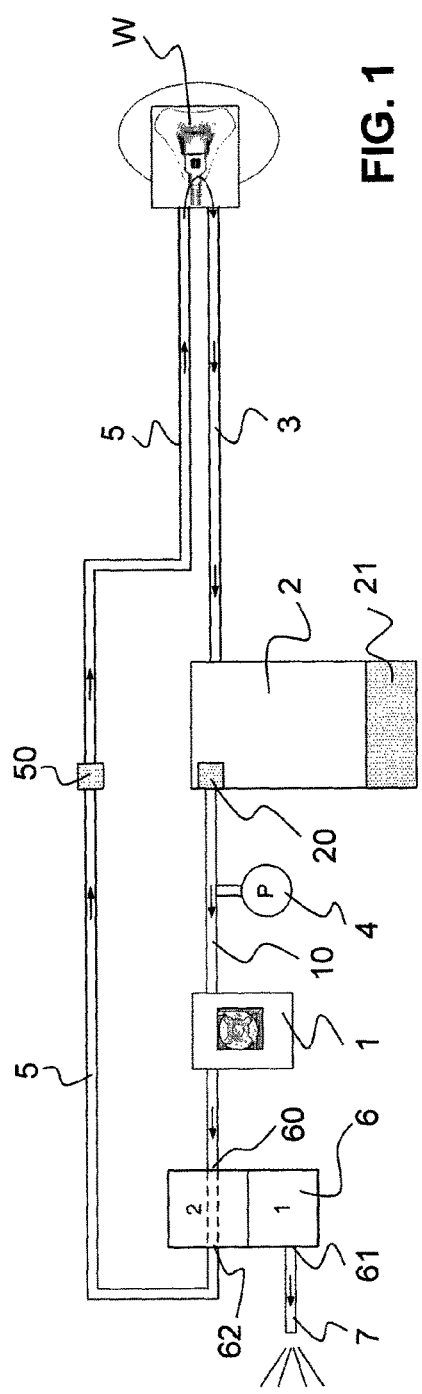
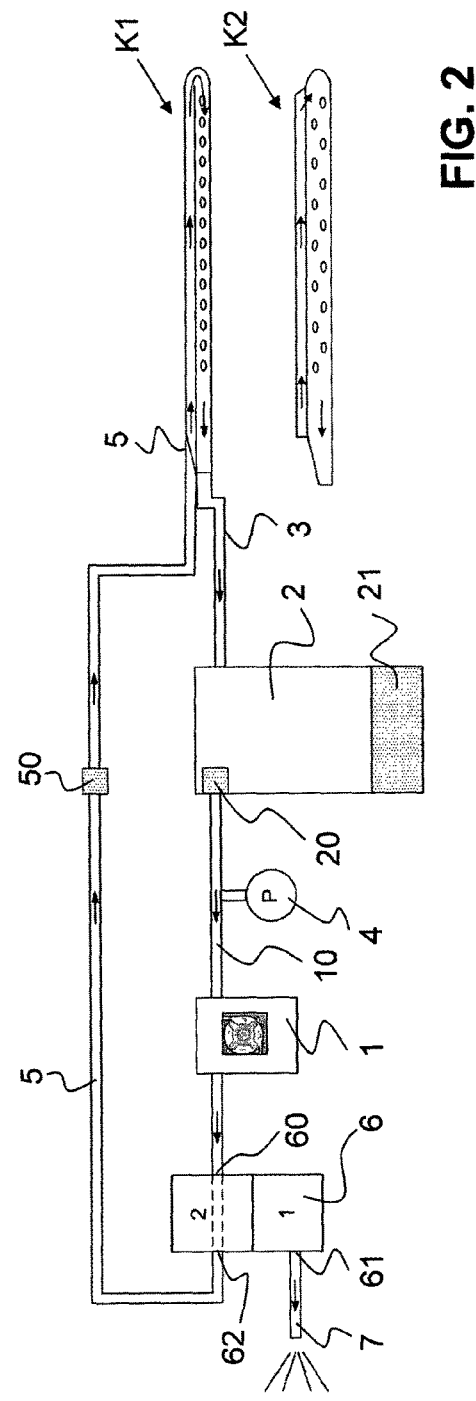
FIG. 1
FIG. 2

SYSTEM FOR ASPIRATING FLUIDS FROM A BODY USING NEGATIVE PRESSURE

CROSS-REFERENCE TO RELATED APPLICATION

The present application is the United States national phase of International Patent Application No. PCT/CH2012/000132, filed Jun. 14, 2013, which application claims priority of Switzerland Application No. 1064/11, filed Jun. 23, 2011. The priority application is incorporated herein by reference.

FIELD OF THE DISCLOSURE

Technical Field

The present invention relates to a system for aspirating fluids from a human or animal body by means of negative pressure, a drainage pump unit, and a method for operating such a system.

Prior Art

Drainage pump systems are used to aspirate body liquids and fluids in the medical field, for example in thorax drainage or in wound drainage, but also during or after surgical interventions or when performing liposuction. These systems usually have a suction pump or vacuum pump, one or more fluid collection containers, and a drainage tube connection between patient and fluid collection container.

With a negative pressure generated in the fluid collection container, fluid or secretion from a cavity in the patient is aspirated through the drainage tube into the collection container and collected therein. Filters arranged at the pump-side outlet of the collection container protect the suction pump from possible contamination by the aspirated fluid.

The fluid collection container can be connected to the pump via an external vacuum hose and via a surge tank, as is disclosed in WO 03/103747, for example. However, it can also be secured releasably on the housing of the drainage pump, as is proposed in US 2009/0163882 and US 2009/0157019, for example. In this case, the vacuum line runs through the interior of the pump housing.

In addition to the drainage line, it is also known to run a service line from the pump to the patient. For example, U.S. Pat. No. 5,738,656 uses a double-lumen tube, in which a first lumen forms the drainage line and the second lumen is an air conduit which, at the patient-side end, opens into the drainage line. In this way, air or gas can be fed into the patient cavity to be aspirated, and the cavity can thus be flushed. This lumen can additionally be used as a measurement line for determining differences in flow or pressure.

In WO 2005/061025, a service line connected to the patient-side end of the drainage tube is likewise used to flush the drainage line, in order to avoid or to eliminate occlusions of the line by aspirated clots or tissue.

US 2011/0071415 also discloses a drainage tube and a separate flushing line.

WO 2010/126444 and WO 2011/037524 relate to a wound drainage system with a flushing line and with an additional pump. This second pump is used to aspirate air from the fluid collection container through the flushing line to the wound and from there through the drainage line back into the fluid collection container.

DISCLOSURE OF THE INVENTION

It is an object of the invention to make available an improved system and an improved drainage pump unit for aspirating fluids.

The system according to the invention for aspirating fluids from a body by means of negative pressure has: a drainage line for removing the fluid from the body, a fluid collection container connected to the drainage line for collecting the aspirated fluid, a pump for generating in the drainage line the negative pressure used to aspirate the fluid, and an auxiliary line whose end near the body is in fluidic communication with an end, near the body, of the drainage line. According to the invention, in the system, a closed or approximately closed circuit is present or can be generated, which interconnects this pump, the auxiliary line, the drainage line and the fluid collection container and through which air or a liquid can be pumped, wherein the auxiliary line can be used for flushing the drainage line.

In order to form the closed or approximately closed circuit, a two-way valve is preferably present in the system, which two-way valve has a first position, in which the connection between pump and auxiliary line is interrupted, such that air aspirated through the pump is released into the environment and the circuit is open. In this position, a negative pressure is built up in the fluid collection container and in the drainage line, and the body fluid is thus aspirated out of the body opening. In a second position of the two-way valve, the connection between pump and auxiliary line is closed and the approximately closed circuit according to the invention is formed.

The circuit is usually only approximately closed, because the drainage line ends in a connector piece which has suction openings towards the wound through which wound liquid can be aspirated. Usually the drainage line and the auxiliary line end in a common catheter or in a common connector piece. Catheters or connector pieces of this kind are known from prior art.

The drainage pump unit according to the invention for use in a system according to the invention has a suction pump for generating a negative pressure which is used to aspirate a fluid and which can be applied in a drainage line connectable to the drainage pump unit. The drainage pump unit can be connected to an auxiliary line whose end near the body is in fluidic communication with an end, near the body, of the drainage line. According to the invention, the drainage pump unit moreover has a two-way valve, wherein the two-way valve serves, in a first position, to release air from the suction pump into the environment and, in a second position, to connect the suction pump to the auxiliary line. In said second position of the two-way valve, the auxiliary line is usable for flushing the drainage line.

This drainage pump unit can comprise the suction pump and the means of controlling the latter. Preferably, it also comprises one or more fluid collection containers, which can be secured on the housing of the suction pump. This drainage pump unit is preferably designed as a portable appliance.

It is a further object of the invention to make available a method for operating such a system, which permits cleaning of the drainage line.

In the method according to the invention for operating such a drainage system, a connection between the pump and the auxiliary line is established through which air flows from the pump through the auxiliary line. In this way, an approximately closed circuit is generated which interconnects this pump, the auxiliary line, the drainage line and the fluid collection container, this air being pumped through the drainage line into the fluid collection container, as a result of which the drainage line is cleaned. Alternatively, a fluid can be pumped through the auxiliary line by means of the pump in order to clean the drainage line. For example, a salt solution is suitable as such a liquid.

When the circuit is closed, except for the mentioned openings in the catheter or the connector piece, the auxiliary line can be used to flush the system, in particular the drainage tube. Air that is output from the vacuum pump into the environment when the circuit is open is now pumped into the auxiliary line. When auxiliary line and drainage line are in fluidic communication with each other at the patient side, the air flushes the drainage line and passes into the fluid collection container. Liquids in the drainage line are thus carried off to the fluid collection container. The flushing of the drainage line with air of a liquid prevents obstruction of the system at an early stage, since secretions are regularly removed from the drainage tube and from any coupling parts, and it is therefore impossible for dried-in columns of fluid to form.

By virtue of the filter in the fluid collection container, contamination of the suction pump is prevented not only during the drainage procedure but also when flushing the system. If the auxiliary line also has one or more filters, contamination of the pump is also avoided on this side. This second filter also prevents particles or contaminants being able to travel from the pump to the wound.

An advantage of this system according to the invention is that a single pump can be used for the drainage and also for the flushing. This reduces the manufacturing costs. By virtue of the single pump, the drainage pump unit can be made relatively small and light, which is advantageous especially in a portable system. At a set pressure level, air is circulated in the second position. The pressure level remains approximately the same during the flushing. This pressure level can correspond to the pressure level during the suction procedure. The speed of the pump controls the speed (intensity) of the air flow without influencing the pressure level.

No external air is used for the flushing. This is desirable especially in the hospital environment, since the risk of introducing external germs into the wound is minimized. It is, however, also possible to pump a liquid instead of air through the auxiliary line to the drainage line in order to clean the system.

It is a further object of the invention to make available a system and a method by which a pressure can be measured in the area of the body cavity.

If a pressure sensor is present, the pressure in the area of the wound or of another body cavity can be easily ascertained. For this purpose, the drainage line is first of all flushed, as described above, and then, with the pump switched off, the pressure in the drainage line and therefore also in the cavity of the body is measured. The pressure sensor can for this purpose be arranged on the container-side outlet of the pump, between fluid collection container and pump, in the fluid collection container or in the drainage line. The sensor is preferably arranged between pump and fluid collection container. It is therefore not necessary to arrange a sensor in the proximity of the wound or in the area of the auxiliary line. The same pressure sensor can be used that also monitors the operation of the pump during the drainage procedure.

Moreover, by virtue of the system according to the invention, an obstruction can be easily detected. If the pressure on the pressure sensor rises during the flushing, the closed circuit is not free and an obstruction must be removed.

The flushing preferably takes place, and the pressure measurement also preferably takes place, automatically and recurrently. The two-way valve can be controlled correspondingly via the control of the pump. It is also advantageous that only one valve has to be activated and that no further pumps or other structural parts are involved. This simplification reduces development and production costs, increases the functional reliability in use and reduces any maintenance work.

The system according to the invention thus successfully removes secretion-based obstructions from the tube system, offers active prevention of obstructions, detects existing obstructions and permits a relatively accurate pressure measurement in the area of the body cavity or of the wound.

The system according to the invention is suitable in particular as a wound drainage system, as a heart drainage system and as a chest drainage system. The other areas of use mentioned at the outset are, however, also possible.

Other embodiments and variants of the method according to the invention are set forth in the dependent claims.

BRIEF DESCRIPTION OF THE DRAWINGS

Preferred embodiments of the invention are described below with reference to the drawings, which serve only for explanatory purposes and are not to be interpreted as limiting the invention. In the drawings:

FIG. 1 shows a schematic representation of the system according to the invention in use during wound drainage, and FIG. 2 shows a schematic representation of the system according to the invention in use during chest and heart drainage.

DESCRIPTION OF PREFERRED EMBODIMENTS

FIG. 1 shows the system according to the invention during wound drainage.

The system has a suction pump 1, preferably a motor-driven electrical vacuum pump, in particular a diaphragm pump of a known type. A fluid collection container 2 is connected to a first outlet of the suction pump 1 via a vacuum line 10, such that a negative pressure generated by means of the pump is established in the container 2. At least one filter 20 is arranged at the pump-side inlet of the fluid collection container 2 in order to avoid contamination of the pump 1. The filter 20 is of a known type, being in particular an overflow filter and/or bacterial filter and/or odour filter. The container 2 can be located outside the pump housing or it can be secured releasably on the latter.

A drainage line 3 opens into the fluid collection container 2, this line 3 connecting the interior of the container 2 to a cavity of a human or animal body. In this example, the cavity is a wound on which a wound cover W is secured. The drainage line 3 leads into this wound cover W or it is secured on a coupling piece arranged on the latter. The known medical hoses, for example made of silicone, are suitable as drainage line 3.

The drainage line 3 can be plugged into the container 2 by means of a suitable connenctor piece. However, as is known from the abovementioned prior art, it can also be plugged into the housing of the pump 1 via a suitable coupling part and connected releasably to the container 2.

A pressure sensor 4 for measuring the pressure in the vacuum line 10 and therefore also in the drainage line 3 is arranged between fluid collection container 2 and pump 1. The sensor 4 can also be arranged at another location, as long as its position is suitable for measuring the pressure in the drainage line 3.

The pump 1 is connected at a second outlet to an inlet 60 of a two-way valve 6. In a first position of the two-way valve 6, a connection is established from the inlet 60 to a first outlet 61 of the valve 6. This outlet 61 forms the air release opening or the exhaust of the system or it leads to such an exhaust via an air release line 7.

In this first position of the two-way valve 6, the pump works as a vacuum pump, with a negative pressure being applied in the fluid collection container 2 and in the drainage line 3, and fluids and secretions being aspirated out of the wound into the container 2. The aspirated secretions are designated by reference sign 21 in FIG. 1.

The two-way valve 6 has a second outlet 62. An auxiliary line 5, also called flushing line, is attached thereto. This auxiliary line 5 likewise leads to the wound, and its wound-side end is in fluidic communication with the wound-side end of the drainage line 3. Both of these ends preferably merge into a common wound-side connector piece. Such connector pieces are known from the prior art. The auxiliary line 5 and the drainage line 3 can be two tubes, in particular of silicone, running completely separate from each other. However, it is also possible that the two tubes are secured to each other at least in sections. Preferably, however, a double-lumen tube is used in which a first lumen forms the drainage line 3 and a second lumen forms the auxiliary line 5. The auxiliary line 5 preferably has a smaller internal diameter than the drainage line 3. The auxiliary line 5 can also serve other purposes, for example for introducing liquids and medicines into the cavity. For this purpose, a separate and closable inlet (not shown here) can be present in the auxiliary line 5.

At least one filter 50 of a known type is preferably arranged in the flushing line 5 in order to prevent contamination of the pump and of the wound. The filter 50 can be arranged at the second outlet 62 of the two-way valve 6.

Known valves are suitable as the two-way valve 6, preferably those that can be activated electronically and that have one inlet and two outlets that can be connected optionally and alternately to the inlet.

When the two-way valve 6 is located in its second position, the connection between the inlet 60 and the first outlet 61 is interrupted, but the connection between inlet 60 and second outlet 62 is established. A closed circuit of the lines 3, 5, 10 is thus formed. Only the openings in the catheter or the connector piece are still present. The circuit extends from the vacuum pump 1 via the two-way valve 6 and the auxiliary line 5 to the wound-side end of the auxiliary line 5 and from there via the drainage line 3 back to the fluid collection container 2, to the vacuum line 10 and to the pump 1. Depending on the nature of the wound-side connector piece, the transition from the auxiliary line 5 to the drainage line 3 can be located at a short distance from the end of the drainage line 3 or directly on this end.

When this circuit is closed, air is no longer released from the vacuum pump 1 into the environment but instead into the auxiliary line 5. This compressed air can be used to flush and clean the system. The circuit of the air is shown by arrows in FIG. 1. The air or liquid pumped through the auxiliary line 5 passes through the drainage line 3 into the fluid collection container 2, in which process any particles and drops that have been left behind are sucked away. If the line is obstructed, the pressure sensor 4 detects a rise in pressure and reports this to a monitoring system controlling the pump 1.

After the flushing in the closed circuit, a pressure measurement can be carried out in the cavity, in particular in the wound. For this purpose, the pump 1 is stopped, and the pressure is measured statically with the pump-internal pressure sensor 4.

The flushing preferably takes place continuously or periodically at different air or liquid speeds. The flushing time, particularly in periodic operation, can be a few seconds to a few minutes. The flushing can be manually triggered by a user. However, the system control is preferably configured such that, during a drainage procedure, flushing is recurrently carried out automatically at defined intervals.

FIG. 2 shows the system according to the invention in use during chest or heart drainage. The system is the same. Identical parts are provided with identical reference signs. However, the drainage line 3 and the auxiliary line 5 end here in a catheter. Two different catheter types K1 and K2 are shown in the figure. Other types of coupling pieces or catheters can likewise be used.

The system according to the invention prevents and removes obstructions in the drainage line and also permits a relatively accurate measurement of the negative pressure in the body cavity.

What is claimed is:

1. System for aspirating fluids from a human or animal body by means of negative pressure, which system has: a drainage line for removing the fluid from the body, a fluid collection container connected to the drainage line for collecting the aspirated fluid, a pump for generating the negative pressure in the drainage line to aspirate the fluid, and an auxiliary line whose end near the body is in fluidic communication with an end, near the body, of the drainage line, wherein in the system, an approximately closed circuit is one of present or can be generated, which interconnects the pump, the auxiliary line, the drainage line and the fluid collection container and through which air or a liquid can be pumped from the pump through the auxiliary line and the drainage line into the fluid collection container, in order to clean the drainage line, wherein the auxiliary line is usable for flushing the drainage hose, and wherein the drainage line and the auxiliary line end in a common catheter or in a common connector piece, and wherein a pressure sensor is arranged between pump and fluid collection container, which measures the pressure in the drainage line.

2. System according to claim 1, wherein the system has a two-way valve for forming the approximately closed circuit.

3. System according to claim 2, wherein the two-way valve has a first position, in which the connection between pump and auxiliary line is interrupted, such that air aspirated through the pump is released into the environment and the circuit is open.

4. System according to claim 3, wherein the two-way valve has a second position, in which the connection between pump and auxiliary line is closed and the circuit is closed.

5. System according to claim 1, wherein the drainage line ends in the fluid collection container, and the pump generates the negative pressure in the fluid collection container.

6. System according to claim 1, wherein a filter is arranged at the pump-side outlet of the fluid collection container.

7. System according to claim 1, wherein the auxiliary line has a filter.

8. System according to claim 1, wherein the pump is a diaphragm vacuum pump.

9. Method for operating a system according to claim 1, which system has: a drainage line for removing the fluid from the body, a fluid collection container connected to the drainage line for collecting the aspirated fluid, a pump for generating in the drainage line the negative pressure to aspirate the fluid, and an auxiliary line whose end near the body is in fluidic communication with an end, near the body, of the drainage line, wherein the drainage line and the auxiliary line end in a common catheter or in a common connector piece, wherein according to said method a connection between the pump and the auxiliary line is established through which air or a liquid flows from the pump through the auxiliary line, as a result of which an approximately closed circuit is generated in the system, wherein the circuit interconnects the pump, the auxiliary line, the drainage line and the fluid collection container, as a result of which this air or the liquid is pumped through the drainage line into the fluid collection container, as a result of which the drainage line is cleaned, and wherein the pressure in the drainage line is measured by means of a pressure sensor arranged between pump and fluid collection container.

10. Method according to claim 9, wherein the pump is stopped after the drainage line has been cleaned, and the pressure in the drainage line is measured by means of a pressure sensor.

11. Method according to claim 9, wherein the connection between pump and auxiliary line is interrupted and, after this interruption, the pump generates a negative pressure in the drainage line for the purpose of aspirating the fluids in the body.

12. Method according to claim 9, wherein establishment and interruption of the connection between pump and auxiliary line take place automatically and recurrently.

* * * * *